United States Patent
Ufkes

(10) Patent No.: US 11,364,314 B2
(45) Date of Patent: Jun. 21, 2022

(54) PORTABLE UV-C DISINFECTION APPARATUS, METHOD, AND SYSTEM

(71) Applicant: UD Innovations, LLC, Sullivan's Island, SC (US)

(72) Inventor: Philip J. Ufkes, Sullivan's Island, SC (US)

(73) Assignee: UD Innovations, LLC, Sullivan's Island, SC (US)

( * ) Notice: Subject to any disclaimer, the term of this patent is extended or adjusted under 35 U.S.C. 154(b) by 240 days.

(21) Appl. No.: 16/814,166

(22) Filed: Mar. 10, 2020

(65) Prior Publication Data

US 2020/0206375 A1  Jul. 2, 2020

Related U.S. Application Data

(63) Continuation-in-part of application No. 15/869,444, filed on Jan. 12, 2018, now Pat. No. 10,583,212.
(Continued)

(51) Int. Cl.
*A61L 2/10* (2006.01)
*A61L 2/24* (2006.01)

(52) U.S. Cl.
CPC ........ *A61L 2/10* (2013.01); *A61L 2/24* (2013.01); *A61L 2202/11* (2013.01);
(Continued)

(58) Field of Classification Search
CPC .......... A61L 2/10; A61L 2/24; A61L 2202/14; A61L 2202/11; A61L 9/20;
(Continued)

(56) References Cited

U.S. PATENT DOCUMENTS

2011/0168898 A1  7/2011  Statham et al.
2015/0217012 A1*  8/2015  Garner ............... A61L 2/24
                                                              422/24
(Continued)

FOREIGN PATENT DOCUMENTS

WO  2007095543 A2  8/2007
WO  2015116876 A1  8/2015
WO  2016044759 A1  3/2016

OTHER PUBLICATIONS

Extended European Search Report, European application No. 18738922.6. dated Sep. 8, 2020. European Patent Office, Munich, DE.
(Continued)

*Primary Examiner* — Sean E Conley
*Assistant Examiner* — Brendan A Hensel
(74) *Attorney, Agent, or Firm* — Gregory Finch; Finch Paolino, LLC

(57) ABSTRACT

A portable UV-C disinfection apparatus, method, and system for ultraviolet germicidal irradiation. UV-C emitters may be coupled to an array housing having a planar array surface in a vertical configuration. UV-C sensors are configured to measure the amount of UV-C light or near UV-C light from a target surface. A controller may be communicably engaged with the UV-C sensors to determine the amount of UV-C radiation collected by the UV-C sensors. The controller includes instructions stored on a memory according to the amount of UV-C radiation collected corresponding to an effective kill-dose for surface disinfection. The improved apparatus, method, and system reduces exposure time by varying the intensity and wavelength of the UV-C administered, while concurrently reducing UV overexposure to surfaces by administering radiation through a rotational zonal application.

18 Claims, 16 Drawing Sheets

Related U.S. Application Data

(60) Provisional application No. 62/445,408, filed on Jan. 12, 2017.

(52) U.S. Cl.
CPC ....... *A61L 2202/14* (2013.01); *A61L 2202/16* (2013.01); *A61L 2202/25* (2013.01)

(58) Field of Classification Search
CPC ........... A61L 2209/111; A61L 2202/25; H05B 47/155; H05B 47/125; H05B 45/20; Y02B 20/40
See application file for complete search history.

(56) References Cited

U.S. PATENT DOCUMENTS

2016/0375163 A1* 12/2016 Hawkins ............. F21V 33/0068
422/22
2017/0173195 A1* 6/2017 Stibich ..................... A61L 2/24

OTHER PUBLICATIONS

First Examination Report, European application No. 18738922.6. dated Jul. 13, 2021. European Patent Office, Munich, DE.
Extended European Search Report, European application No. 187389303.8 dated Dec. 11, 2020 European Patent Office, Munich, DE.

* cited by examiner

PORTABLE UV-C DISINFECTION APPARATUS, METHOD, AND SYSTEM

CROSS-REFERENCE TO RELATED APPLICATIONS

This application is a continuation-in-part of U.S. patent application Ser. No. 15/869,444, filed on Jan. 12, 2018 entitled "PORTABLE UV-C DISINFECTION APPARATUS, METHOD, AND SYSTEM", which claims the benefit of U.S. Provisional Application Ser. No. 62/445,408, filed on Jan. 12, 2017 entitled "PORTABLE UV-C DISINFECTION APPARATUS, METHOD, AND SYSTEM", the disclosure of each of which is hereby incorporated in its entirety at least by reference.

FIELD

The present invention relates to methods and devices for bacterial, fungal and/or viral sterilization and disinfection, and is more particularly directed to a portable UV-C disinfection apparatus and system for ultraviolet germicidal irradiation.

BACKGROUND

Ultraviolet germicidal irradiation (UVGI) is a disinfection method that uses short-wavelength ultraviolet (UV-C) light to kill or inactivate microorganisms. One mechanism by which UV-C deactivates microorganisms is by destroying nucleic acids and disrupting their DNA, leaving them unable to perform vital cellular functions. The administration of UV-C radiation is becoming widely adopted by many hospitals as a more effective and reliable means of surface disinfection, as compared to the use of chemical cleaning agents alone. The effectiveness of germicidal UV-C irradiation depends on factors such as the length of time a microorganism is exposed to UV-C, the intensity and wavelength of the UV-C radiation, the presence of particles that can protect the microorganisms from UV, and a microorganism's ability to withstand UV-C during its exposure. In air and surface disinfection applications, the UV effectiveness is estimated by calculating the UV dose to be delivered to the microbial population. A method of calculating UV dose is as follows: UV dose $\mu Ws/cm^2$=UV intensity $\mu W/cm^2 \times$ Exposure time (seconds).

Germicidal UV for disinfection is most typically generated by a mercury-vapor lamp. Low-pressure mercury vapor has a strong emission line at 254 nm, which is within the range of wavelengths that demonstrate strong disinfection effect. The optimal wavelengths for disinfection are close to 265 nm. UV-C LEDs use semiconductors to emit light between 255 nm-280 nm. The wavelength emission is tunable by adjusting the material of the semiconductor. The use of LEDs which emit a wavelength more precisely tuned to the maximal germicidal wavelength results in greater microbe deactivation per amp of power, maximization of microbial deactivation for the available, less ozone production, and less materials degradation. Although the germicidal properties of ultraviolet (UV) light have long been known, it is only comparatively recently that the antimicrobial properties of visible violet-blue 405 nm light have been discovered and used for environmental disinfection and infection control applications. A large body of scientific evidence is now available that provides underpinning knowledge of the 405 nm light-induced photodynamic inactivation process involved in the destruction of a wide range of prokaryotic and eukaryotic microbial species, including resistant forms such as bacterial and fungal spores. Violet-blue light, particularly 405 nm light, has significant antimicrobial properties against a wide range of bacterial and fungal pathogens and, although germicidal efficacy is lower than UV light, this limitation is offset by its facility for safe, continuous use in occupied environments.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

An object of the present disclosure is a portable UV-C disinfection apparatus comprising an array housing having a substantially planar array surface; a plurality of UV-C emitters coupled to the substantially planar array surface, the plurality of UV-C emitters being coupled to the substantially planar array surface in a substantially vertical configuration in relation to each other; at least one UV-C sensor coupled to the substantially planar array surface; at least one orientation sensor coupled to the array housing; a base housing, the base housing defining an interior portion; a motor being housed in the interior portion of the base housing, the array housing being coupled to a shaft of the motor at a bottom portion of the array housing; a controller being housed in the base housing, the controller being operably engaged with the motor, the at least one orientation sensor, the plurality of UV-C emitters, and the at least one UV-C sensor; and, a battery pack being housed in the base housing, the battery pack being operably engaged with the motor, the controller, the plurality of UV-C emitters, and the at least one UV-C sensor.

Another object of the present disclosure is a method for room disinfection using UV-C radiation comprising delivering, with a planar array of UV-C emitters, a beam of UV-C radiation to a first zone of a room; receiving, with at least one UV-C sensor, an amount of UV energy reflected from the first zone of the room; measuring, with a processor, a UV energy threshold for the at least one UV-C sensor; rotating, with an electric motor, the planar array of UV-C emitters to a second zone of the room in response to satisfying a UV energy threshold received by the at least one UV-C sensor; delivering, with the planar array of UV-C emitters, a beam of UV-C radiation to the second zone of the room; receiving, with the least one UV-C sensor, an amount of UV energy reflected from the second zone of the room; measuring, with the processor, a UV energy threshold in the second zone for the at least one UV-C sensor; rotating, with the electric motor, the planar array of UV-C emitters to an $N^{th}$ zone of the room in response to satisfying a UV energy threshold received by the at least one UV-C sensor.

Yet another object of the present disclosure is a system for room disinfection using UV-C radiation comprising at least one portable UV-C disinfection apparatus, the at least one portable UV-C disinfection apparatus comprising an array housing having a substantially planar array surface; a plurality of UV-C emitters coupled to the substantially planar array surface, the plurality of UV-C emitters being coupled to the substantially planar array surface in a substantially vertical configuration in relation to each other; at least one UV-C sensor coupled to the substantially planar array surface; at least one orientation sensor coupled to the array housing; a base housing, the base housing defining an interior portion; a motor being housed in the interior portion of the base housing, the array housing being coupled to a shaft of the motor at a bottom portion of the array housing; a controller being housed in the base housing, the controller being operably engaged with the motor, the at least one orientation sensor, the plurality of UV-C emitters, and the at least one UV-C sensor; a battery pack being housed in the base housing, the battery pack being operably engaged with the motor, the controller, the plurality of UV-C emitters, and the at least one UV-C sensor; a remote interface, the system interface being communicably engaged with the controller of the at least one portable UV-C disinfection apparatus; and, a database, the database being communicably engaged with the controller of the at least one portable UV-C disinfection apparatus and the system interface.

Certain aspects of the present disclosure provide for a germicidal disinfection apparatus comprising a housing assembly comprising a base housing and an array housing; a motor being housed in the base housing and configured to rotate the array housing from at least one first orientation to at least one second orientation; a plurality of emitters comprising an array and being housed in the array housing, the plurality of emitters comprising at least one first emitter configured to emit ultraviolet light at a wavelength between 100 to 280 nanometers; at least one second emitter configured to emit visible light at a wavelength between 400 and 410 nanometers; a controller being operably engaged with the plurality of emitters to modulate a duty cycle of the at least one first emitter and the at least one second emitter; wherein the controller comprises at least one processor and at least one non-transitory computer-readable medium having instructions stored thereon that, when executed, cause the processor to perform one or more operations, the one or more operations comprising modulating a duty cycle of the at least one first emitter; modulating a duty cycle of the at least one second emitter; and modulating a pulse width of the at least one first emitter and the at least one second emitter such that the at least one first emitter and the at least one second emitter are configured to pulse emissions of ultraviolet light and visible light, respectively, in phase or out of phase.

In certain embodiments, the germicidal disinfection apparatus may be further configured wherein the at least one first emitter and the at least one second emitter are configured to independently emit radiation in response to a control signal by the controller so as to produce a dual wavelength emission. The controller may be further configured wherein the one or more operations further comprise calculating a radiation dose delivered by the at least one first emitter and the at least one second emitter at one or more zonal orientation.

In certain embodiments, the germicidal disinfection apparatus may further comprise at least one ranging sensor being coupled to a surface of the housing assembly and being communicably engaged with the controller. The germicidal disinfection apparatus may further comprise at least one dual-band radiation sensor being coupled to a surface of the housing assembly and being communicably engaged with the controller. The germicidal disinfection apparatus may further comprise at least orientation sensor being communicably engaged with the controller. In certain embodiments, controller may be further configured wherein the one or more operations further comprise modulating a duty cycle of the at least one first emitter and the at least one second emitter in response to an input from the at least one ranging sensor. The controller may be further configured wherein the one or more operations further comprise calculating a radiation dose delivered by the at least one first emitter and the at least one second emitter in response to an input from the at least one dual-band radiation sensor; and engaging the motor to rotate the array housing from a first zonal orientation to a second zonal orientation. The one or more operations further comprise determining one or more zonal orientation in response to an input from the at least orientation sensor.

Certain aspects of the present disclosure provide for a method for controlling microorganisms in an interior environment comprising positioning a germicidal disinfection apparatus in a first location of the interior environment; pulsing, in a first zonal orientation, an emission from the at least one first emitter and the at least one second emitter; and pulsing, in a second or subsequent zonal orientation, an emission from the at least one first emitter and the at least one second emitter. In accordance with some embodiments, the method for controlling microorganisms may further comprise modulating, with the controller, the pulse width of the at least one first emitter or the at least one second emitter according to a kinetic model associated with at least one bacteria, virus, or fungus. The method may further comprise calculating, with the controller, the kinetic model according to one or more physical characteristics of the interior environment.

Further aspects of the present disclosure provide for a germicidal disinfection apparatus comprising a housing assembly comprising a base housing and an array housing; a motor being housed in the base housing and configured to rotate the array housing 360 degrees around an axis; a plurality of emitters comprising an array of LEDs having a beam angle of less than or equal to 180 degrees, the plurality of emitters comprising at least one first emitter configured to emit ultraviolet light at a wavelength between 100 to 280 nanometers; at least one second emitter configured to emit visible light at a wavelength between 400 and 410 nanometers; a controller being operably engaged with the plurality of emitters to modulate a duty cycle of the at least one first emitter and the at least one second emitter; wherein the controller comprises at least one processor and at least one non-transitory computer-readable medium having instructions stored thereon that, when executed, cause the processor to perform one or more operations, the one or more operations comprising modulating a duty cycle of the at least one first emitter; modulating a duty cycle of the at least one second emitter; modulating a pulse width of the at least one first emitter and the at least one second emitter such that the at least one first emitter and the at least one second emitter are configured to pulse emissions of ultraviolet light and visible light, respectively, in phase or out of phase; and engaging the motor to rotate the array housing between two or more zonal orientations; wherein each zonal orientation in the two or more zonal orientations comprises an emission zone corresponding to the beam angle of the plurality of emitters.

In accordance with certain embodiments, the germicidal disinfection apparatus may further comprise at least one dual-band radiation sensor being coupled to a surface of the housing assembly and being communicably engaged with the controller. The controller may be configured wherein the one or more operations further comprise calculating a radiation dose delivered by the at least one first emitter and the at least one second emitter in response to an input from the at least one dual-band radiation sensor. The one or more operations may further comprise engaging the motor to rotate the array housing between two or more zonal orientations in response to calculating the radiation dose.

Still further aspects of the present disclosure provide for a germicidal disinfection system comprising a germicidal disinfection apparatus comprising a housing assembly comprising a base housing and an array housing; a motor being housed in the base housing and configured to rotate the array housing from a first zonal orientation to a second zonal orientation; a plurality of emitters comprising an array and being housed in the array housing, the plurality of emitters comprising at least one first emitter configured to emit ultraviolet light at a wavelength between 100 to 280 nanometers; at least one second emitter configured to emit visible light at a wavelength between 400 and 410 nanometers; a controller being operably engaged with the plurality of emitters to modulate a duty cycle of the at least one first emitter and the at least one second emitter; wherein the controller comprises at least one processor and at least one non-transitory computer-readable medium having instructions stored thereon that, when executed, cause the processor to perform one or more operations, the one or more operations comprising modulating a duty cycle of the at least one first emitter; modulating a duty cycle of the at least one second emitter; and modulating a pulse width of the at least one first emitter and the at least one second emitter such that the at least one first emitter and the at least one second emitter are configured to pulse emissions of ultraviolet light and visible light, respectively, in phase or out of phase; and a mobile electronic device being communicably engaged with the controller to command one or more mode of operation of the germicidal disinfection apparatus.

In accordance with certain embodiments, a mode of operation of the germicidal disinfection apparatus may comprise one or more operations for modulating the duty cycle of the at least one first emitter and the at least one second emitter according to a kinetic model comprising an effective radiation kill dose for at least one bacteria, virus, or fungus. In some embodiments, a mode of operation of the germicidal disinfection apparatus may comprise one or more operations for modulating a pulse width of the at least one first emitter and the at least one second emitter according to a kinetic model comprising an effective radiation kill dose for at least one bacteria, virus, or fungus.

In some embodiments, the one or more operations of the processor may further comprise operations for calculating a radiation dose delivered by the at least one first emitter and the at least one second emitter; and engaging the motor to rotate the array housing from the first zonal orientation to the second zonal orientation.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Figures 1A, 1B:
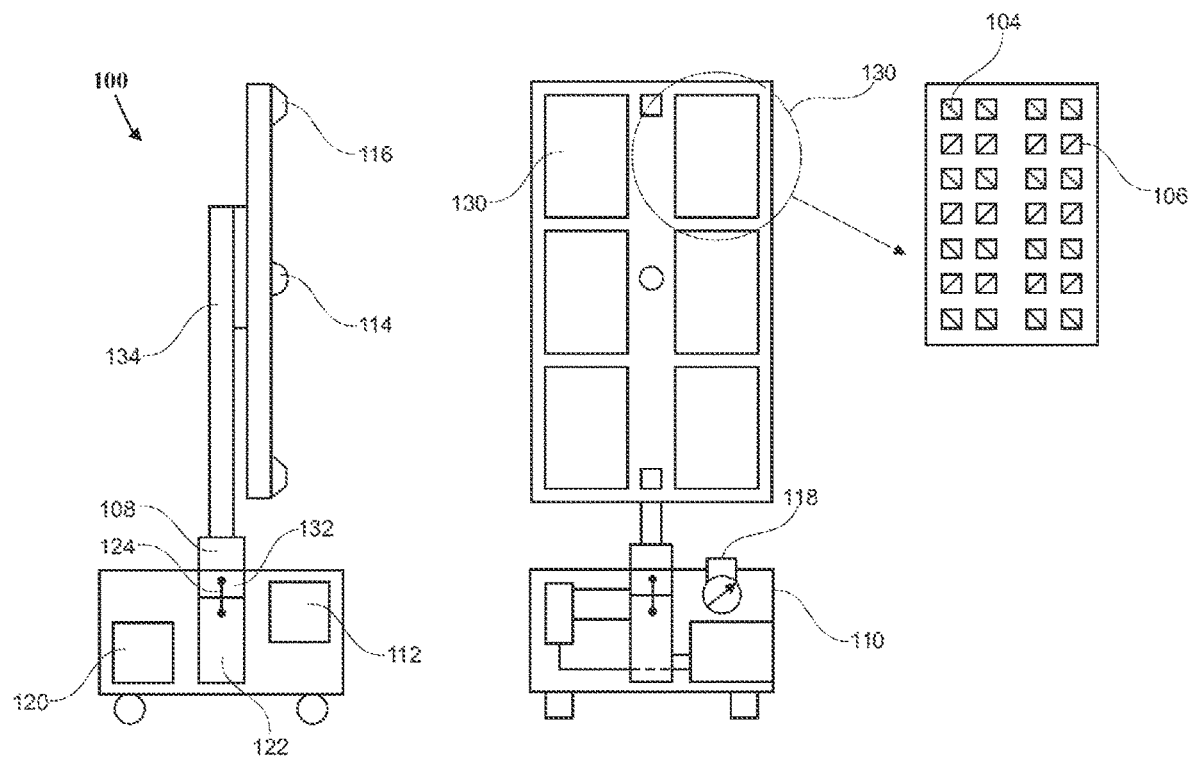
FIG. 1A is a side view of a portable UV-C disinfection apparatus, according to an embodiment.
FIG. 1B is a front perspective view of a portable UV-C disinfection apparatus, according to an embodiment.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems configured to provide for a UV-C disinfection apparatus that reduces exposure time by varying the intensity and wavelength of the UV-C administered, while concurrently reducing UV overexposure to surfaces by administering radiation through a rotational zonal application.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

Figure 1C:
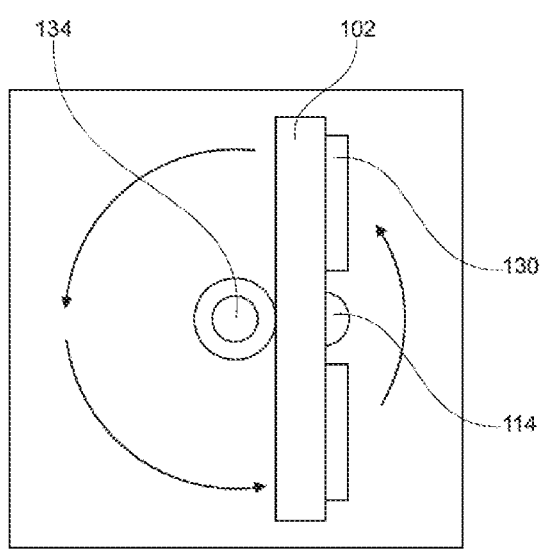
FIG. 1C is a top down view of a portable UV-C disinfection apparatus, according to an embodiment.

Turning now descriptively to the drawings, in which similar reference characters denote similar elements throughout the several views, FIGS. 1A-1C are functional diagrams of a portable UV-C disinfection apparatus 100. According to an embodiment, portable UV-C disinfection apparatus 100 is generally comprised of an array housing 102, one or more UV-C emitters 104, one or more near UV emitters 106, a slip ring 108, a base housing 110, a controller 112, one or more UV-C sensors 114, a ranging sensor 116, an orientation sensor 118, a battery pack 120, a motor 122, motor shaft 124, one or more emitter arrays 130, an encoder 132, and an array support 134. Array housing 102 is coupled to base housing 110 via array support 134, which is coupled to motor shaft 124. Slip ring 108 is operably coupled to array support 134 via motor shaft 124, and functions to provide electrical connections between the components in array housing 102 and battery pack 120, as well as functions as a system bus between the components in array housing 102 and controller 112. Slip ring 108 is operable to enable array support 134 to rotate in a continuous 360-degree rotation via motor shaft 124 while maintaining circuity connections with battery pack 120 and controller 112. Array housing 102 may be constructed of rigid or flexible material, such as plastic, metal, metal alloy, and the like. Base housing 110 provides a stationary foundation for apparatus 100, and may comprise wheels for ease of transportation and positioning. According to an embodiment, one or more UV-C emitters 104, one or more near UV emitters 106, UV-C sensor 114, and ranging sensor 116, are coupled to a face portion of the array housing 102. In an embodiment, UV-C emitters 104 and near UV emitters 106 are preferably UV-C and/or visible light LEDs. In an alternative embodiment, UV-C emitters 104 and near UV emitters 106 are electronic gas-discharge lamps including but not limited to low-pressure mercury-vapor lamps, high-pressure mercury vapor lamps, xenon lamps, mercury-xenon lamps, pulsed-xenon lamps, and deuterium lamps. In another embodiment, UV-C emitters 104 and near UV emitters 106 may be CFL lamps and halogen lamps. Emitters 104 and near UV emitters 106 may be distributed in a linear arrangement over a 48-inch or 24-inch planar surface. Emitters 104 and near UV emitters 106 may be distributed in groups defining an emitter array 130. The linear arrangement of UV-C emitters 104 and near UV emitters 106 direct UV-C radiation in a targeted beam, enabling higher intensity emission with less power consumption as compared to an omnidirectional bulb—thereby enabling power to be supplied by a battery source, such as battery pack 120. The higher intensity generated by focusing a beam of UV-C radiation using a linear array, rather than an omnidirectional transmission generated by a mercury-vapor bulb or a circular LED array, has the dual benefits of reducing exposure time in the dosage calculation and conserving energy. In a preferred embodiment, UV-C emitters 104 are calibrated to have a wavelength emission of 265 nm, and near UV emitters 106 are calibrated to have a wavelength emission of 405 nm (which falls on the visible light spectrum). However, both emitters may be calibrated to various wavelength emissions within a known range of wavelengths that demonstrate strong disinfection effect. UV-C sensor 114 is a closed loop sensor operable to measure the amount of UV-C light or near UV light reflected from the target surface back to UV-C sensor 114. UV-C sensor 114 may be a single sensor or an array of multiple sensors, and may be either integral to array housing 102 or distributed in a target room. UV-C sensor 114 may be a dual band sensor comprised of a single carrier operable to measure UV-C radiation wavelengths of about 265 nm and near UV of about 405 nm. UV-C sensor 114 is operably engaged with controller 112 to communicate the amount of UV-C radiation (single or dual band) collected by UV-C sensor 114. Controller 112 has a set of instructions stored thereon to measure a "kill dose" according to the amount of reflected UV-C radiation collected by UV-C sensor 114 and kill dose parameters stored in memory. Controller 112 may calibrate various kill dose thresholds depending on the specific disinfection application. For example, viruses may require a lower kill dose, while bacteria may require a higher kill dose, and spores may require yet a higher kill dose.

Controller 112 may operate in communication with ranging sensor 116 to more accurately measure a kill dose delivered from emitters 104 and near UV emitters 106. The UV-C energy collected by UV-C sensor 114 might not accurately represent the amount of UV-C energy reflected by the target surface due to the distance, or air gap, between the target surface and UV-C sensor 114. This is due to the fact that UV-C radiation loses intensity as a function of distance travelled; therefore, the measured reflected energy at UV-C sensor 114 is less than the energy actually reflected by the target surface by a function of the distance between the target surface and UV-C sensor 114. Ranging sensor 116 may be operably engaged with controller 112 to calculate an "air gap compensation" to virtually relocate UV-C sensor 114 to the nearest object. This can be accomplished mathematically by correcting for the reduction in UV-C energy as a function of distance, as well as other variables such as temperature and humidity. Ranging sensor 116 is operably engaged to detect the distance to the nearest object in the zone of each UV-C sensor 114. Ranging sensor 116 may be comprised of, for example, one or more sensors capable of detecting the presence and location of objects within the sensor range without physical contact, such as sonic ranging, scanning ranging, and/or visible or infrared-based light sensors. Controller 112 may adjust the kill dose threshold of reflected energy received by UV-C sensor 114 in accordance with the distance input defined by ranging sensor 116. In the absence of ranging sensor 116, controller 112 may enable a manual input by a user to define the desired air gap adjustment.

Controller 112 may be positioned within an interior portion of base housing 110 or array housing 102. Battery pack 120 may be positioned within an interior portion of base housing 110 and is operable to provide all components of portable UV-C disinfection apparatus 100. Orientation sensor 118 is coupled to an interior or exterior portion of array housing 102, and is operable to enable controller 112 to detect unit location, array orientation, and zone position of UV-C disinfection apparatus 100. Orientation sensor 118 may be comprised of one or more motion sensors, real-time clocks, RFID, GPS, accelerometers, magnetic compass, gyroscopes, piezoelectric sensors, piezoresistive sensors, and capacitive orientation-sensing components or any other suitable means or orientation and location functioning; or any combination thereof.

Figure 1D:
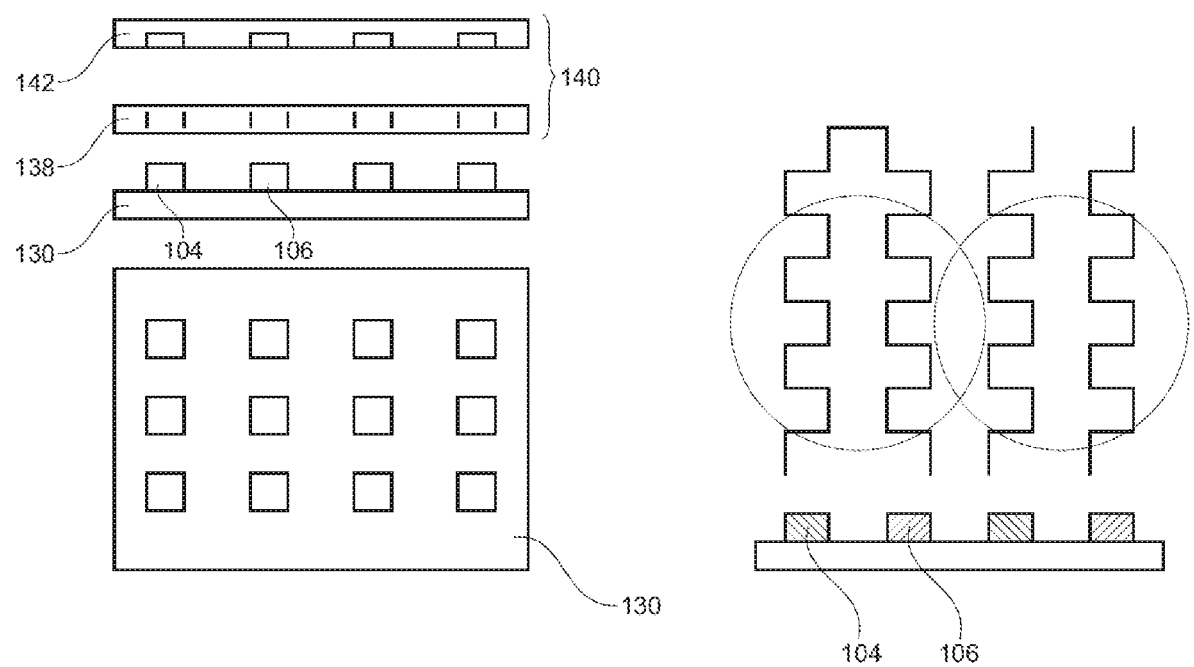
FIG. 1D is an exploded view of a lens assembly of a portable UV-C disinfection apparatus, according to an embodiment.

Referring now to FIG. 1D, emitter array 130 may further comprise a lens assembly 140. Lens assembly 140 may be comprised of a heat sink or reflector 138 and a lens 142. Lens assembly 140 functions to protect UV-C emitters 104 and near UV emitters 106 from damage, dissipate heat from emitters 104 and 106, and direct light in a desired angle (e.g. 120 degrees). Heat sink 138 functions to remove heat from UV-C emitters 104 and near UV emitters 106 to prevent overheating through conduction, and dissipate heat from heat sink 138 to the environment through convention and/or conduction. Heat sink 138 may be constructed of any suitable thermally conductive material. Lens 142 may be coupled to heat sink 138, and may function to protect UV-C emitters 104 and near UV emitters 106 from physical contact and environmental damage, such as dust accumulation. Lens 142 may be constructed from any UV-C transmittable material (for example, Acrylite); and, may be configured as a Fresnel lens such that lens 142 may be substantially planar in shape.

As discussed above, UV-C emitters 104 and near UV emitters 106 emit radiation at wavelengths of 265 nm and 405 nm respectively. Each wavelength displays its own kinetics of a kill curve for target microorganisms. It is anticipated that UV-C emitters 104 and near UV emitters 106 may pulse emission in-phase (i.e. emit light at the same time), or out of phase (i.e. emit light at opposite times), or operate independently, which may modify the kinetics of each wavelength's respective kill curve, such that a dual wavelength emission will reduce the overall time required to achieve a kill dose as compared to a single wavelength emission. Likewise, various modulation schema may be employed between UV-C emitters 104 and UV-C emitters 106 in order to optimize the kinetics of the kill curve for a given microorganism (e.g. viruses, bacteria, and spores), thereby reducing the amount of time required to achieve a kill dose for the target microorganism.

Figure 2:
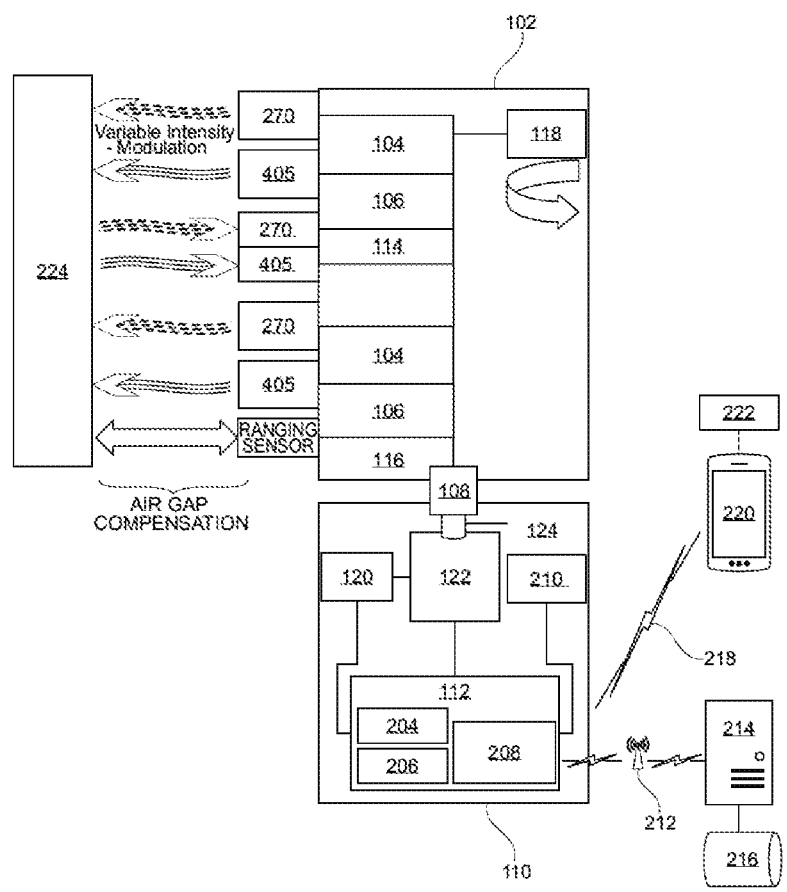
FIG. 2 is a system diagram of a portable UV-C disinfection system, according to an embodiment.

Referring now to FIG. 2, a system diagram of a portable UV-C disinfection system is shown. According to an embodiment, portable UV-C disinfection apparatus 100 administers UV-C radiation to a target zone via one or more UV-C emitters 104 and one or more near UV emitters 106. In a preferred embodiment, as mentioned above, UV-C emitters 104 are calibrated to emit short wave UV-C radiation at a wavelength of 265 nm, and near UV emitters 106 are calibrated to have a wavelength emission of 405 nm, or vice versa. Remote interface 220 is communicably engaged with controller 112 via a wireless communication interface, such as Bluetooth or WiFi. Remote interface 220 may be a tablet computer, smart phone, laptop computer, wireless I/O device, and the like. Remote interface 220 associates a room identifier 222 with a target room for disinfection. Remote interface 220 may include a user workflow configured to validate that a target room is prepped properly for disinfection and that all the steps in the disinfection workflow have been completed. A room identifier 222 may be a scanned barcode or RFID tag. Remote interface 220 communicates a request to begin a disinfection cycle to controller 112. Processor 204 processes the request to begin a disinfection cycle. Processor 204 executes instructions to orientation sensor 118 to determine a position and orientation in the target room. Processor 204 executes instructions for ranging sensor 116 to scan a Zone N 224 to determine the closest object in the target room. The data from orientation sensor 118 and ranging sensor 116 is stored in memory 206, along with room ID 222. Processor 204 executes instructions to measure air gap compensation to calibrate UV-C sensor 114 according to the data from ranging sensor 116. Processor 204 executes instructions to initiate UV-C emitters 104 and near UV emitters 106 to emit UV-C radiation to target Zone N 224. Radiation reflected from target Zone N 224 is reflected back to array housing 102 and is collected by UV-C sensor 114. UV-C sensor 114 sends UV dosage data to processor 204. Processor 204 executes instructions to measure a kill dose according to UV reflectivity data and air gap compensation variables. Once a threshold dosage value has been received by UV-C sensor 114, processor 204 executes instructions to discontinue UV-C emission by UV-C emitters 104 and near UV emitters 106 and rotate array housing to the next consecutive zone. Processor 204 executes instructions to store dosage data from Zone N 224 in memory. Processor 204 executes instructions to engage motor 122, thereby turning motor shaft 124 to rotate array housing 102 such that UV-C emitters 104 and near UV emitters 106 are oriented to the next consecutive zone. Slip ring 108 is the relay and the system bus between the components in array housing 102 and battery pack 120; and is the system bus between the components in array housing 102 and controller 112. Slip ring 108 enables array housing 102 to rotate in a 360-degree range of motion with motor shaft 124; however, the desired rotation may be calibrated to less than 360-degrees. Once array housing 102 has been rotated to the next zone, processor 204 executes the same instructions as those of Zone N 224 to deliver radiation to the next zone and measure a kill dose based on reflected radiation. This process is continued until UV-C emitters 104 and near UV emitters 106 have delivered a kill dose in a full 360-degree rotation (or the desired angular zones).

Processor 204 executes instructions to store dosage data from each zone in memory 208. The dosage data is time stamped, and communicated to hospital server 214 using wireless communication chip set 208 via hospital network 212. Hospital server 214 stores information retrieved from controller 112 in hospital database 216. This information can be utilized by hospital server 214 to determine the health of the hospital, as well as monitor the health and status of a facility wide deployment. Communication chip set 208 may be a LoRa chipset, and hospital network 212 may be configured as a low power wide area network (LPWAN) to reduce burden on the hospital's Wi-Fi network. LoRa is a wireless modulation for long-range, low-power, low-data-rate applications. LoRa is based on chirp spread spectrum modulation which maintains low-power characteristics and significantly increases communication range. LoRa commonly operates in the unlicensed frequency bands of 867-869 MHz and 902-928 MHz, although other frequency bands under 1000 MHz may be commonly utilized. Processor 204 may communicate a confirmation to remote interface 220 to confirm disinfection of the target room is complete.

Figure 3:
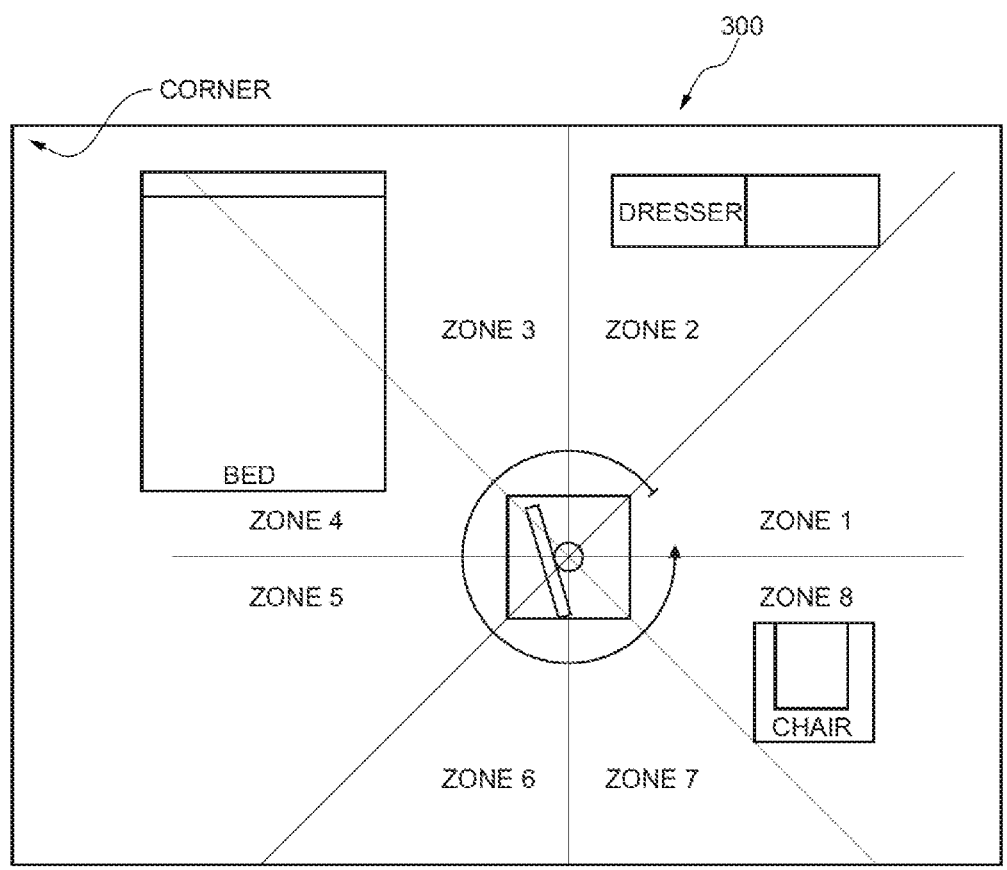
FIG. 3 is a schematic diagram of disinfection zones of a portable UV-C disinfection system, according to an embodiment.

Referring now to FIG. 3, a functional diagram of a portable UV-C disinfection system is shown. According to an embodiment, UV-C disinfection apparatus 100 is positioned in a target room for disinfection. UV-C disinfection apparatus 100 is operable to process a room identifier, orientation inside the room, and the desired zones for disinfection. The identity of the target room and the orientation of UV-C disinfection apparatus 100 within the target room may be determined by Real-Time Clock, RFID or other means to identify the room, GPS and other location methods, inertial navigation, magnetic navigation and other orientation methods. The UV-C sensors measure the UV-C energy reflected from the target zone. The ranging sensors measure the distance to the nearest object in the zone, and virtually relocate the UV-C sensors to the location of the nearest object to compensate for the air gap between the surface of the nearest object and the surface of the UV-C sensor. The UV-C emitters deliver UV-C light in a first zone, e.g. Zone 1. Due to the varying distance and reflectivity of zone surfaces and objects, the UV-C sensors may receive reflected energy at varying rates between zones. Reflective paints or reflective adhesive sheets may be used on hospital walls to increase the rate of UV-C reflectivity of the walls. Once a target area is disinfected, i.e. has received a kill dose, the array stores the zone dosage information and rotates the array to the next consecutive zone, e.g. Zone 2. Information regarding the orientation of objects in the zones and room location is saved in the memory of the UV-C disinfection apparatus. UV-C disinfection apparatus 100 may be programmed to exclude zones in certain spaces, e.g. "keep out zones." Likewise, UV-C disinfection apparatus 100 may be programmed to disinfect non-successive zones in a predetermined disinfection path. UV-C disinfection apparatus 100 delivers radiation in a predetermined path until all zones (in this illustration Zones 1-8) have received a kill dose, as measured by the reflected energy at the UV-C sensors. In a preferred embodiment, the area of each zone and intensity of UV-C emission is calculated such that UV-C disinfection apparatus 100 is operable to deliver a kill-dose to all desired zones by continuous rotation. Upon delivering a kill dose to all desired zones, the disinfection cycle is concluded and a confirmation is communicated to the remote interface and hospital server. The data collected during the disinfection cycle, such as air gap compensation, keep-out zones, disinfection path, and dosage allocation, is stored in the UV-C disinfection apparatus memory under a unique room identifier. This data may be acquired by a hospital server to monitor the health and status of a facility wide deployment.

Figure 4:
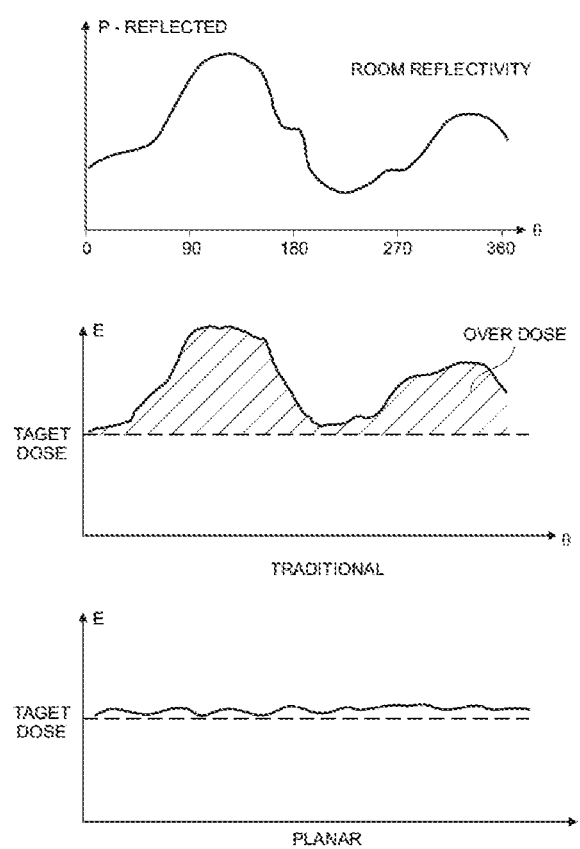
FIG. 4 is an illustration of UV-C emission plots comparing prior art solutions to embodiments of the present disclosure.

FIG. 4 further illustrates the concepts from FIG. 3; in particular, the ability of the present disclosure to solve the problem of over exposure of UV-C radiation during a UV-C disinfection process, as compared to the prior art. Prior art solutions emit UV-C radiation in an omnidirectional pattern. A kill dose is measured when a threshold amount of reflected energy is measured at the UV-C sensor on the UV-C disinfection apparatus. Since a target room exhibits different rates of reflectivity at different locations within the room, a UV-C disinfection apparatus that administers radiation in an omnidirectional pattern is reliant on the least reflective surface in the room to measure a kill dose at the UV-C sensor. Embodiments of the present disclosure, as discussed above, administer radiation and measure reflected energy on a per zone basis; thereby delivering only the necessary amount of radiation required for a particular zone, and not more. This dramatically reduces the overall amount of excess radiation delivered to the target room, as embodiments of the present disclosure enable emission of radiation and measurement of reflected energy specifically in the target zone.

Figure 5:
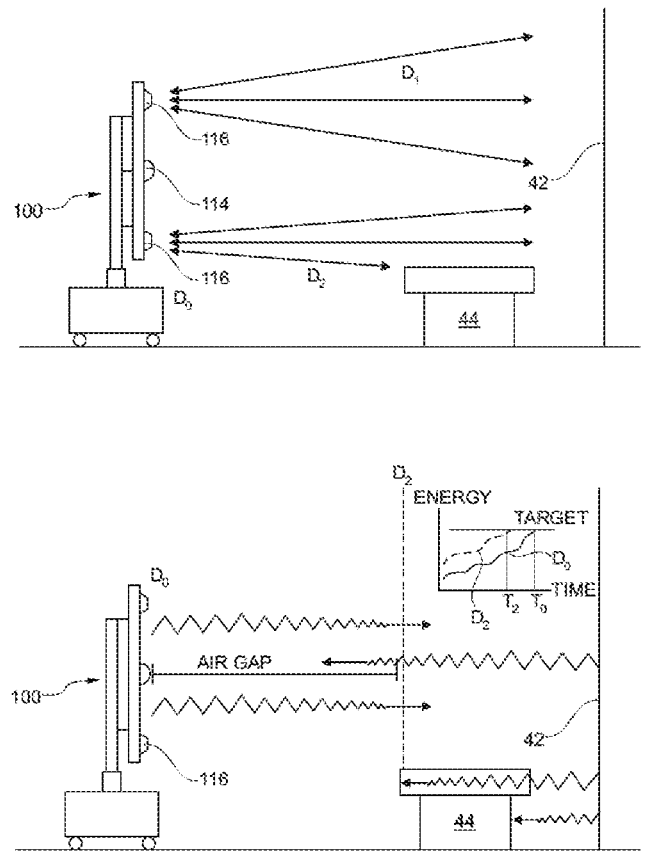
FIG. 5 is an illustration of an air gap compensation calculation, according to an embodiment.

Referring now to FIG. 5, a functional illustration of an air gap compensation calculation by UV-C disinfection apparatus 100 is shown. According to an embodiment, ranging sensor 116 measures the distance from UV-C disinfection apparatus 100, $D_0$, to the target surface, $D_1$, and to the leading surface of the closest object in the room, $D_2$. The distance $D_2$ defines the air gap between the UV-C sensors 114 and the leading surface of the closest object in the room 44. The back side of object 44, i.e. the "dark" side of the object relative to UV-C disinfection apparatus 100, is disinfected by receiving UV-C radiation reflected back from the target surface 42. As discussed above, a kill dose is measured by the amount of radiation reflected from the target surface 42 to UV-C sensors 114. The kill dose is measured using reflected radiation, rather than direct energy, in order to ensure that the dark side of surfaces in the target room (i.e. surfaces not receiving direct exposure of UV-C radiation) are sufficiently disinfected. The amount of reflected radiation only needs to be measured from the leading edge of the closest object in the room 44 to measure a kill dose on the dark side of object 44. The space between $D_0$ and $D_2$ represents the air gap between UV-C sensors 114 and the leading edge of the closest object in the room 44. The intensity of the reflected radiation is reduced between $D_2$ and $D_0$, as the intensity of radiation diminishes with distance. Therefore, measuring a kill dose at $D_0$ results in an over measurement of radiation, which in turn results in overexposure UV-C radiation and increased time for UV-C disinfection apparatus 100 to complete a disinfection cycle. UV-C disinfection apparatus 100 mitigates over-exposure and minimizes disinfection time by virtually relocating UV-C sensors 114 to distance $D_2$ by executing an air gap compensation algorithm. This enables UV-C disinfection apparatus 100 to measure the minimum required amount of reflected UV-C radiation necessary for an effective kill dose.

Figure 6:
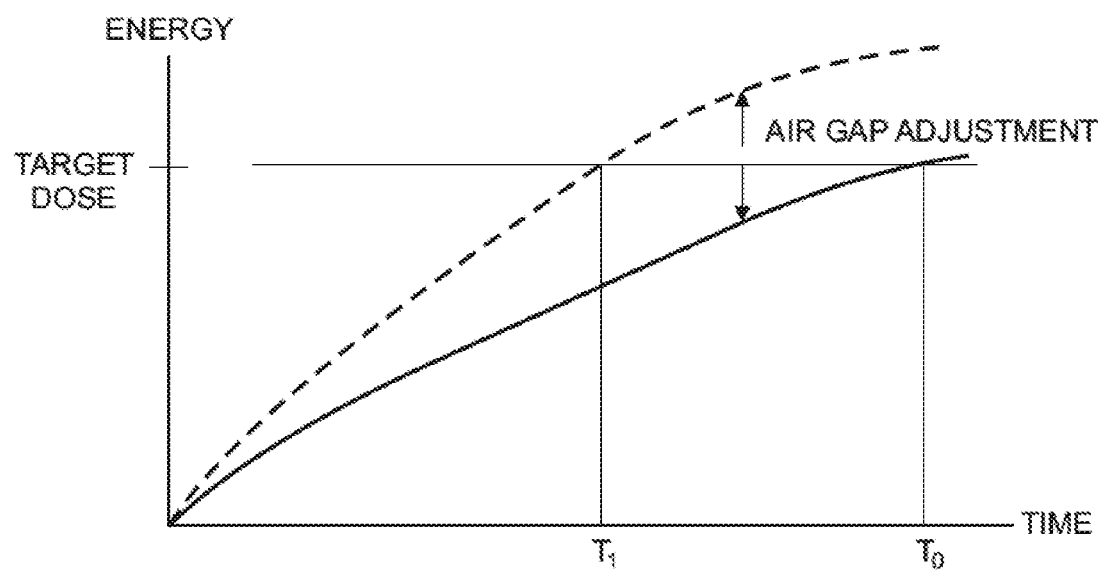
FIG. 6 is an illustration of target dose calculation, as calculated with and without compensation for air gap.

FIG. 6 further illustrates the above concepts of FIG. 5 by plotting the reflected energy received by UV-C sensors 114 (on the y-axis) as a function of time (on the x-axis) in order to reach a target dose of reflected energy. Where UV-C sensors 114 have not been virtually relocated to compensate for air gap, the time required to reach an effective kill dose is shown on the graph as $T_0$. Where UV-C sensors 114 have been virtually relocated to compensate for air gap, the time required to reach an effective kill dose is shown on the graph as $T_1$. The delta between $T_0$ and $T_1$ represents the amount of time saved during the disinfection cycle when compensating for air gap between the UV-C sensor and the location of the nearest object in the zone.

Figure 7:
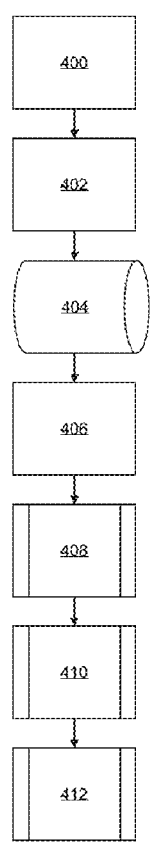
FIG. 7 is a process flow diagram of a room disinfection using a portable UV-C disinfection system, according to an embodiment.

Referring now to FIG. 7, a process flow diagram of a room disinfection using a portable UV-C disinfection system is shown. According to an embodiment, the portable UV-C disinfection system identifies the room 400 by receiving an identification tag, such as an RFID label, or other location information, such as GPS, and stores this room ID in memory 402. The room ID is communicated to a remote interface and through a network to a hospital database 404. A user positions the portable UV-C disinfection system in a room 406 and sends a command to the portable UV-C disinfection system via a remote interface to begin the disinfection cycle 408. The portable UV-C disinfection system verifies no occupants are present in the room 410, and once safety has been verified, the UV-C disinfection system begins the disinfection cycle 412.

Figure 8:
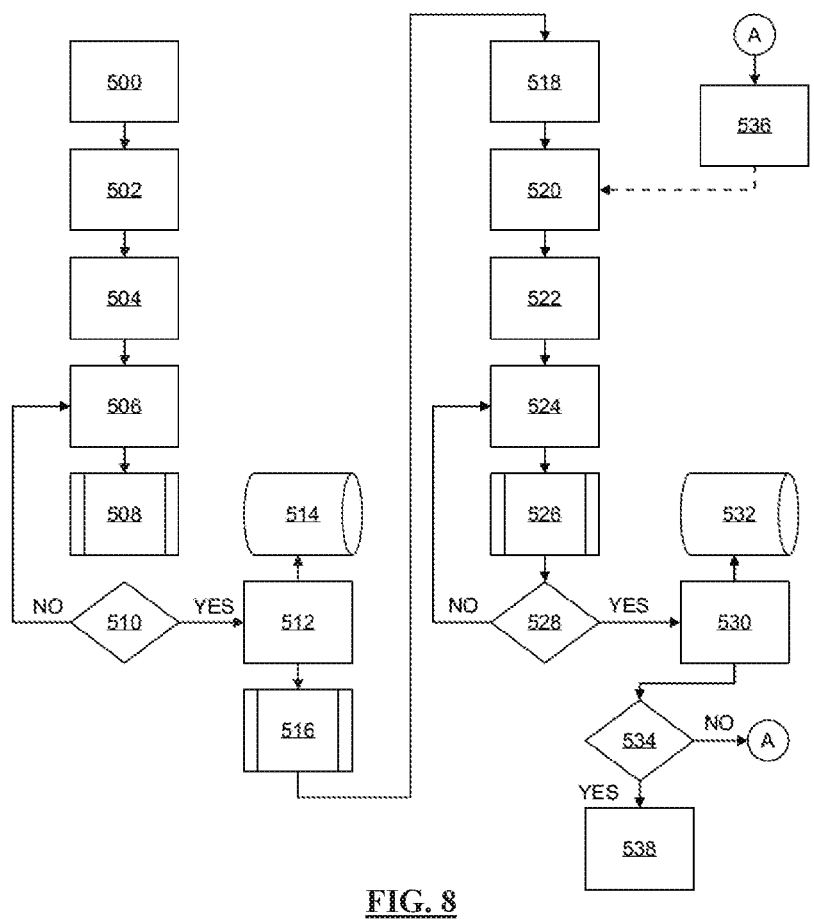
FIG. 8 is a process flow diagram of a zone disinfection by a portable UV-C disinfection system, according to an embodiment.

Referring now to FIG. 8, a flow diagram of a zone disinfection by a portable UV-C disinfection system is shown. According to an embodiment, the portable UV-C disinfection system signals the ranging to scan Zone 1 500, and calculates the distance between a UV-C sensor and the nearest object in the zone to determine air gap compensation 502 for the UV-C sensor. The UV-C emitters deliver radiation to Zone 1 504 in dual wavelengths of about 265 nm and about 405 nm. The UV-C sensors receive reflected radiation 506 from the target zone to continuously measure dosage 508. As the sensors receive reflected UV-C radiation, a decision is made as to whether or not the calculated dosage strength for a zone has been met 510, i.e. a kill dose has been administered. If "NO," the UV-C sensors continue to monitor radiation 506 and radiation is delivered until the calculated dosage for the zone has been achieved. Once the sensors receive a threshold radiation value, the UV-C emitters discontinue radiation and Zone 1 disinfection is concluded 512. The UV-C disinfection system stores dosage data in memory 514 along with room identifying information. Upon completion of Zone 1 disinfection, the array rotates to Zone 2 516.

Ranging sensors scan Zone 2 518 and calculate the distance between the UV-C sensor and the nearest object in the zone to determine air gap compensation 520 for the UV-C sensor. Alternatively, a predetermined air gap compensation parameter may be calibrated in the system. The UV-C emitters deliver radiation to Zone 2 522 in dual wavelengths of about 265 nm and about 405 nm. The UV-C sensors receive reflected radiation 524 from the target zone to continuously measure dosage 526. As the sensors receive reflected UV-C radiation, a decision is made as to whether a kill dose for the zone has been delivered 528. If "NO," the UV-C sensors continue to receive reflected radiation 524 from the target zone to continuously measure dosage 526. If "YES," the sensors have received a threshold radiation value, the UV-C emitters discontinue radiation and Zone 2 disinfection is concluded 530. The UV-C disinfection system stores dosage data in memory 532 along with room identifying information.

Upon the completion of a zone disinfection, the system processing ranging and orientation data from sensors to determine if the 360-degree rotation is complete 534. If "NO," sensors begin 536. If the information from the ranging and orientation sensors indicate a complete rotation of 360 degrees and disinfection of all zones, then the cycle is complete 538. Once a disinfection cycle is complete, the portable UV-C disinfection system signals the remote interface of the completion and stores system data related to the disinfection in the device database.

Figure 9:
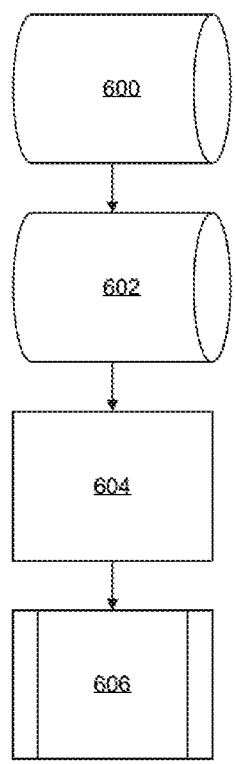
FIG. 9 is a process flow diagram of the utilization of data from a zone disinfection by a portable UV-C disinfection system, according to an embodiment.

FIG. 9 illustrates the utilization of data from a zone disinfection by a portable UV-C disinfection system. According to an embodiment, the portable UV-C disinfection system receives data from the UV-C, ranging, and orientation sensors. This data provides information as to the orientation of objects in a room and the time and dosage strength needed to disinfect a room. The data is stored in the portable UV-C disinfection system memory 600. The data is time-stamped to keep a record of when a room was disinfected 602. This time-stamped data is then communicated via a network to a hospital server 604. The received time-stamped information is then associated with a room identification and stored in a hospital database 606. This information can be utilized by quality control to determine the health of the hospital, as well as monitor the health and status of a facility wide deployment.

Figure 10:
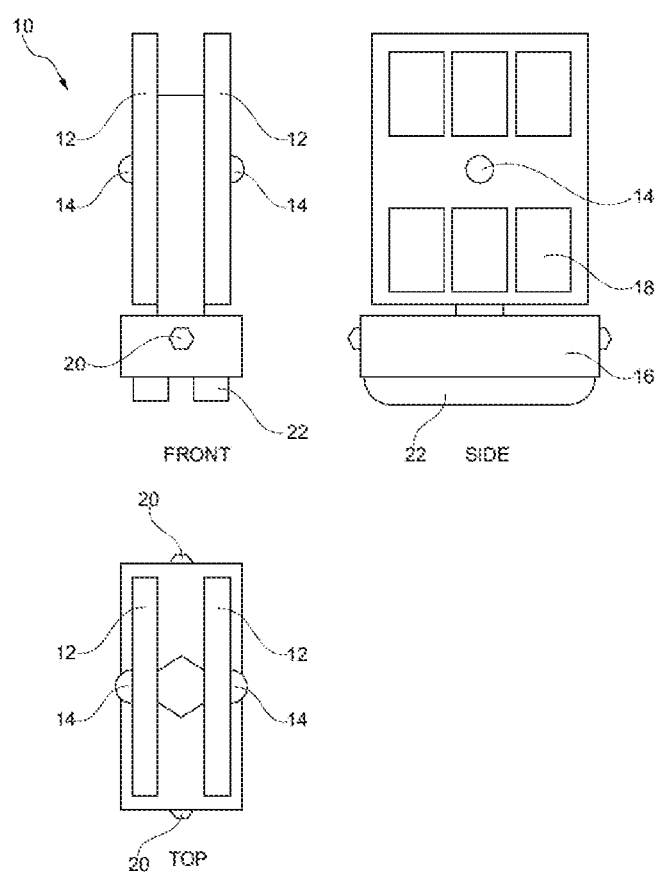
FIG. 10 is a front, side, and top view of an alternative embodiment of a portable UV-C disinfection system.
Figure 11:
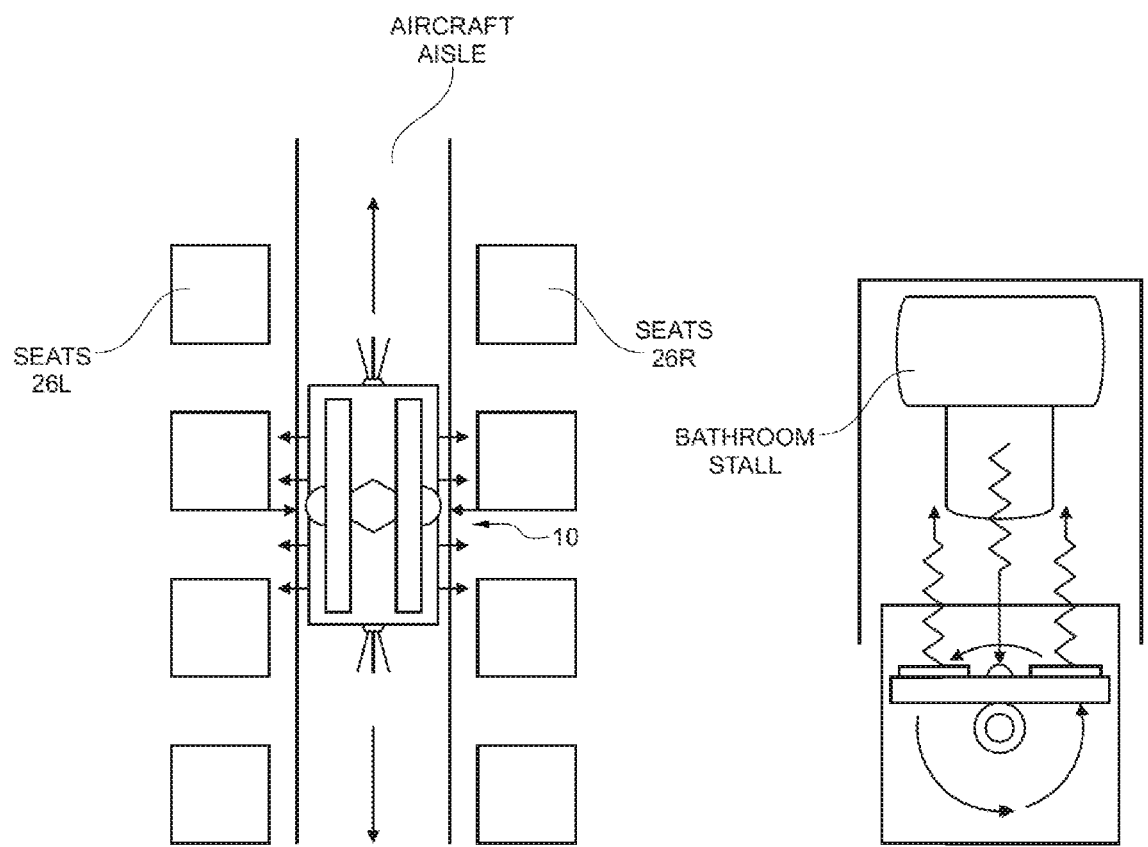
FIG. 11 is a functional diagram of disinfection of the interior of an aircraft, according to an embodiment.

Referring now to FIG. 10, a front, side, and top view of an alternative embodiment of a portable UV-C disinfection system is shown. According to an embodiment, a UV-C disinfection apparatus 10 is generally comprised of a left and a right array surface 12, a left and a right UV-C sensor 14, a front and a rear proximity sensor 20, a base housing 16, a left and a right emitter array 18, and tracks 22. UV-C disinfection apparatus 10 may function to emit UV-C radiation in substantially the same way as described in FIG. 1 above, including the application of dual band radiation. As opposed to rotating in a 360-degree range of motion as described above, UV-C disinfection apparatus 10 emits radiation in a fixed transmission pattern from left and right array surface 12. As shown in FIG. 11, UV-C disinfection apparatus 10 is operable to disinfect the interior of an aircraft by moving down an aircraft aisle 24 using tracks 22. Left emitter array 18 delivers radiation to left seats 26L, and right emitter array 18 delivers radiation to right seats 26R. Left and right UV-C sensors 14 measure the amount of reflected energy received from left emitter array and right emitter array 18, respectively. Once a kill dose has been measured for a target zone in the aircraft, UV-C disinfection apparatus 10 continues down aircraft aisle 24 using tracks 22. Front and rear proximity sensors 20 prevent UV-C disinfection apparatus 10 from making contact with objects in its path.

Figure 12:
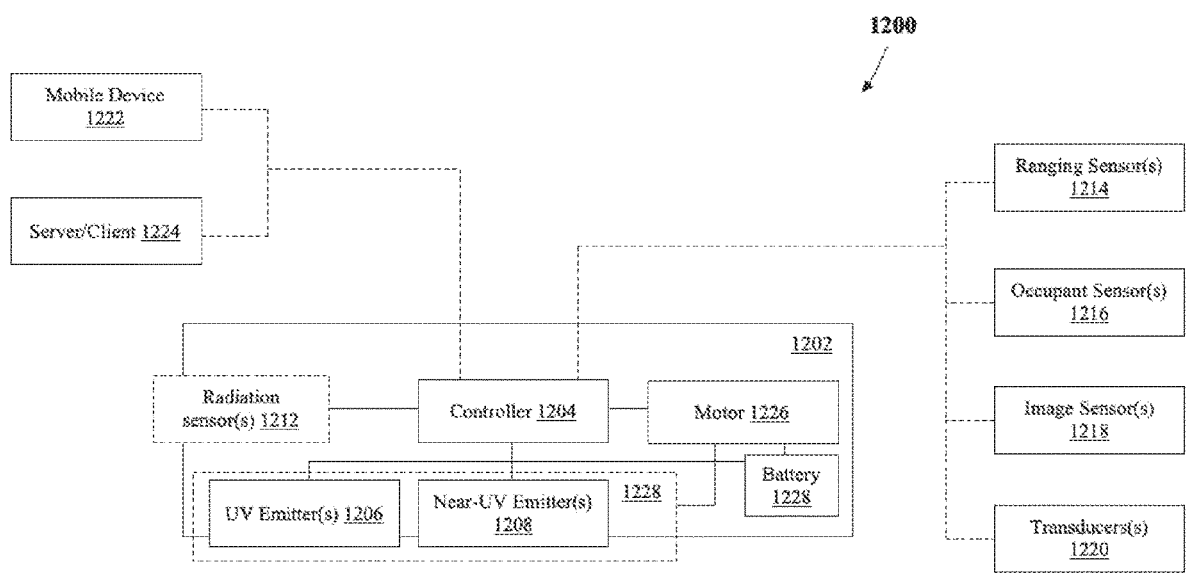
FIG. 12 is a functional block diagram of an apparatus and system for germicidal disinfection, in accordance with an embodiment.

Referring now to FIG. 12, a functional block diagram of a germicidal disinfection apparatus and system 1200 is shown. In accordance with an embodiment, a germicidal disinfection apparatus and system 1200 may comprise a housing assembly 1202, a controller 1204, at least one UV emitter(s) 1206, at least one near-UV emitter(s) 1208, a motor 1226 and a battery 1228. Housing assembly 1202 may comprise an array housing or array surface 1228 configured to position UV emitters 1206 and near-UV emitters 1208 in a planar and/or substantially vertical orientation. UV emitters 1206 may comprise a plurality of LEDs configured as an array. The plurality of LEDs may comprise one or more LEDs configured to produce a spectral output within a UV-A region (315-400 nanometers (nm)), a UV-B region (280-315 nm), and/or a UV-C region (100-280 nm). In certain embodiments, UV emitters 1206 comprises one or more LEDs configured to produce a spectral output within a UV-C region, and more particularly in a range of 250-270 nm. Near-UV emitters 1208 may comprise a plurality of LEDs configured as an array. Near-UV emitters 1208 may be configured to produce a visible light output within a near-UV region (e.g. 400-410 nm). In certain embodiments, near-UV emitters 1208 may be configured to produce a visible light output having a spectral wavelength of 405 nm. UV emitters 1206 and near-UV emitters 1208 may comprise a plurality of LEDs configured as an array.

In accordance with certain embodiments, motor 1226 may be operably engaged with battery 1228, controller 1204, and array housing 1228 to rotate array housing 1228 around an axis to two or more different zonal orientations. A zonal orientation may be defined by a beam angle of UV emitters 1206 and near-UV emitter 1208. For example, if UV emitters 1206 and near-UV emitter 1208 have a beam angle of 45 degrees, then an interior room would comprise eight emission zones (e.g., as shown in FIG. 3).

In accordance with certain embodiments, controller 1204 may be operably engaged with UV emitters 1206 and near-UV emitters 1208 via an electrical relay. Controller 1204 may comprise a processor and a memory device having instructions stored thereon to cause the processor to execute one or more control functions of controller 1204 to modulate a duty cycle of UV emitters 1206 and/or near-UV emitters 1208; modulate a pulse width of UV emitters 1206 and/or near-UV emitters 1208; and control/vary the phase of emission for UV emitters 1206 and/or near-UV-emitters 1208. For example, FIG. 12A shows a pulse wave 1301 of UV emitters 1206 and a pulse wave 1303 of near-UV emitters 1208 being modulated by controller 1204 to pulse a dual-band emission of UV radiation and near-UV radiation in-phase, in a first control setting, and out of phase, in a second control setting.

In accordance with certain embodiments, controller 1204 is operable to control emission of UV emitters 1206 and near-UV emitters 1208 according to one or more operating modes. For example, in an illustrative first mode of operation controller 1204 may be configured to modulate an emission of UV radiation and/or near-UV radiation from UV emitters 1206 and near-UV emitters 1208. In certain embodiments, the first mode of operation may be configured to pulse an emission from UV emitters 1206 and near-UV emitters 1208. In certain embodiments, controller 1204 is configured in the first mode of operation to modulate an emission of UV radiation and near-UV radiation from UV emitters 1206 and near-UV emitters 1208 to produce a dual band emission of radiation, either in-phase or out of phase. In certain embodiments, the first mode of operation may include pulsing the emission of UV radiation and near-UV radiation from UV emitters 1206 and near-UV emitters 1208 simultaneously (i.e. in phase) or in rapid or close succession (i.e. out of phase). In further configurations, the first mode of operation may include pulsing an emission from UV emitters 1206 and disengaging an emission from near-UV emitters 1208 in accordance with a first control setting; and pulsing an emission from near-UV emitters 1208 and disengaging an emission from UV emitters 1206 during a second control setting. In the second mode of operation, controller 1204 may be configured to control and engage an emission of near-UV radiation from near-UV emitters 1208 and disengage a UV emission from UV emitters 1206.

In accordance with certain embodiments, controller 1204 may be communicably engaged with one or more radiation sensor 1212. Radiation sensor(s) 1212 may be coupled to, or otherwise contained within, housing 1202 and/or may be located independent from housing assembly 1202 and communicably engaged with controller 1204 via a wireline or a wireless interface. Certain embodiments may comprise multiple radiation sensors 1212 being integral to housing assembly 1202 and/or separate from housing assembly 1202. Radiation sensors 1212 may comprise one or more closed-loop UV sensors, one or more closed-loop near-UV sensors, and/or one or more dual-band closed loop sensor being operable to measure both UV radiation and near-UV radiation. In an embodiment, radiation sensors 1212 may be configured and arranged such that radiation sensors 1212 are operable to measure an amount of UV radiation and near-UV radiation emitted from UV emitters 1206 and near-UV-emitters 1208 being reflected back to radiation sensors 1212 from a target surface of an interior room. Radiation sensors 1212 may provide a sensor input to controller 1212 in response to receiving the reflected radiation from the target surface of the interior room.

Controller 1204 may be configured to calculate an aggregate amount of radiation received by the target surface in response to the sensor input and determine whether a radiation threshold or target dose of radiation (i.e. a kill dose) has been delivered by UV emitters 1206 and/or near-UV emitters 1208 to the target surface. The radiation threshold or target dose of radiation may be calculated from a kinetic model or dose-response curve corresponding to a group of microorganisms (e.g., bacteria) or a specific microorganism (e.g., *Staphylococcus aureus*). Controller 1204 may have a plurality of target dose data stored in memory and may be configured to calculate a specific radiation threshold in response to a user configuration or other control input. Each kinetic model may include a dose-response curve for single band radiation (e.g. only UV radiation or only near-UV radiation) and dual band radiation (e.g. both UV radiation and near-UV radiation being emitted either in phase or out of phase, or otherwise in succession over a given time period). In certain embodiments, controller 1204 may be configured to calculate a radiation dose according to the kinetic model in response to a input from radiation sensors 1212 to determine whether a threshold dose for a given zone has been delivered. If a threshold dose has been delivered, controller 1204 may be configured to engage the motor to position array surface 1228 to a new emission zone. If all zones have received a threshold dose, controller 1204 may be configured to terminate emission. Controller 1204 may be configured to store radiation data and other operational data in memory and/or communicate radiation data and other operational data to mobile device 1222 and/or server/client device 1224 via a communications interface.

Figure 13A:
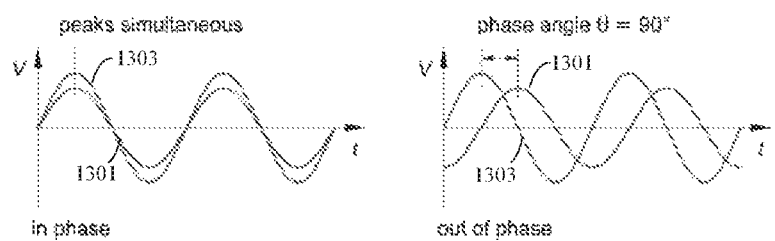
FIG. 13A is a sine wave plot of a UV emission and a near-UV emission being pulsed in-phase and out of phase.
Figure 13B:
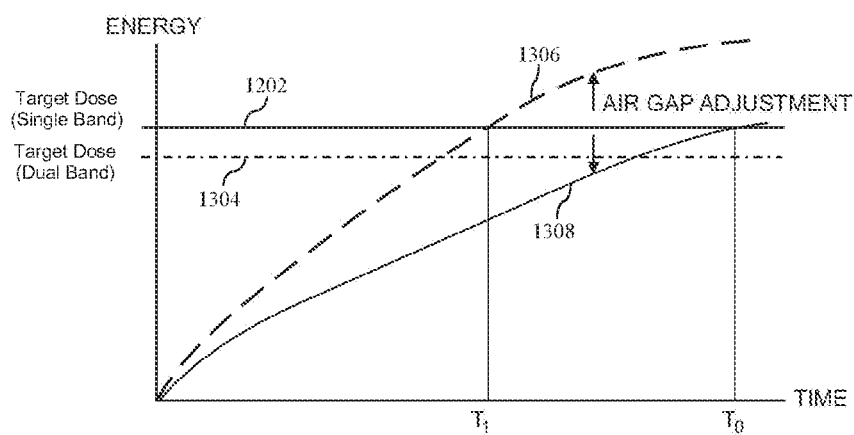
FIG. 13B is a plot of a target dose calculation for a single band emission and a dual band emission, as calculated with and without compensation for air gap.

In certain embodiments, controller 1204 may be communicably engaged with a ranging sensor 1214 being configured to measure a distance between the UV emitters 1206 and near-UV emitters 1208 and a target surface (for example, as shown and described in FIG. 5). Controller 1204 may be configured to process inputs from ranging sensor 1214 and calculate an amount of reflected energy lost as a function of distance to update the kinetic model to calculate a kill dose. For example, FIG. 13B shows an exemplary kinetic model comprising a dose-response curve 1306, a modified dose-response curve 1308 in response to a ranging sensor input, a single band target dose 1302, and a dual band target dose 1304.

In accordance with certain embodiments, controller 1204 may be communicably engaged with an occupant sensor 1216 configured to detect the presence of a person in an interior room in which system 1200 is installed and/or detect the proximity of a person to an emission zone of UV emitters 1206. Occupant sensor 1216 may include one or more sensor types, including but not limited to infrared sensors (IR), ultrasonic sensors, tomographic motion detection sensors, microwave sensors, camera-based sensors, environmental sensors (e.g. temperature, humidity and CO2 sensors), and the like. Controller 1204 may be configured to terminate an emission of UV emitters 1206 in response to an input from occupant sensor 1216 indicative of a person being in an interior room and/or in proximity to an emission zone of UV emitters 1206. In certain embodiments, controller 1204 may be communicably engaged with at least one image sensor 1218;

for example, a digital camera. Image sensor 1218 may function as ranging sensor 1214 and/or occupant sensor 1216. Image sensor 1218 may provide image data to controller 1204 indicative of one or more situational or environmental conditions of an interior location. For example, controller 1204 may be configured to process image data to determine an occupant load of an interior space. Image sensor 1218 may be configured to capture body temperature data of occupants within an interior space. Controller 1204 may be configured to process body temperature data to determine a likelihood of one or more functional load for in the interior space (i.e., the likelihood and scope of microorganisms in the interior space) and estimate a target dose of UV radiation and/or near-UV radiation for the target space. In certain embodiments, controller 1204 is communicably engaged with at least one acoustic transducer 1220. Acoustic transducer 1220 may be configured to capture one or more sound inputs and communicate audio signal data to controller 1204. Controller 1204 may be configured to process audio signal data to determine one or more situational or environmental conditions of the interior space for the purpose of engaging or configuring one or more control settings of germicidal disinfection apparatus and system 1200.

In accordance with certain embodiments, controller 1204 may be communicably engaged with a mobile electronic device 1222 and/or a server/client device 1224 via a wireless or wireline communications interface. Mobile electronic device 1222 and/or server/client device 1224 may be configured to provide a user interface for configuring one or more control settings for controller 1204. Controller 1204 may be configured to communicate device data, sensor data, and usage data for mobile electronic device 1222 and/or server/client device 1224. Mobile electronic device 1222 and/or server/client device 1224 may be configured to communicate external data to controller 1204 to configure one or more control settings and/or update or provide one or more kinetic model.

Figure 14:
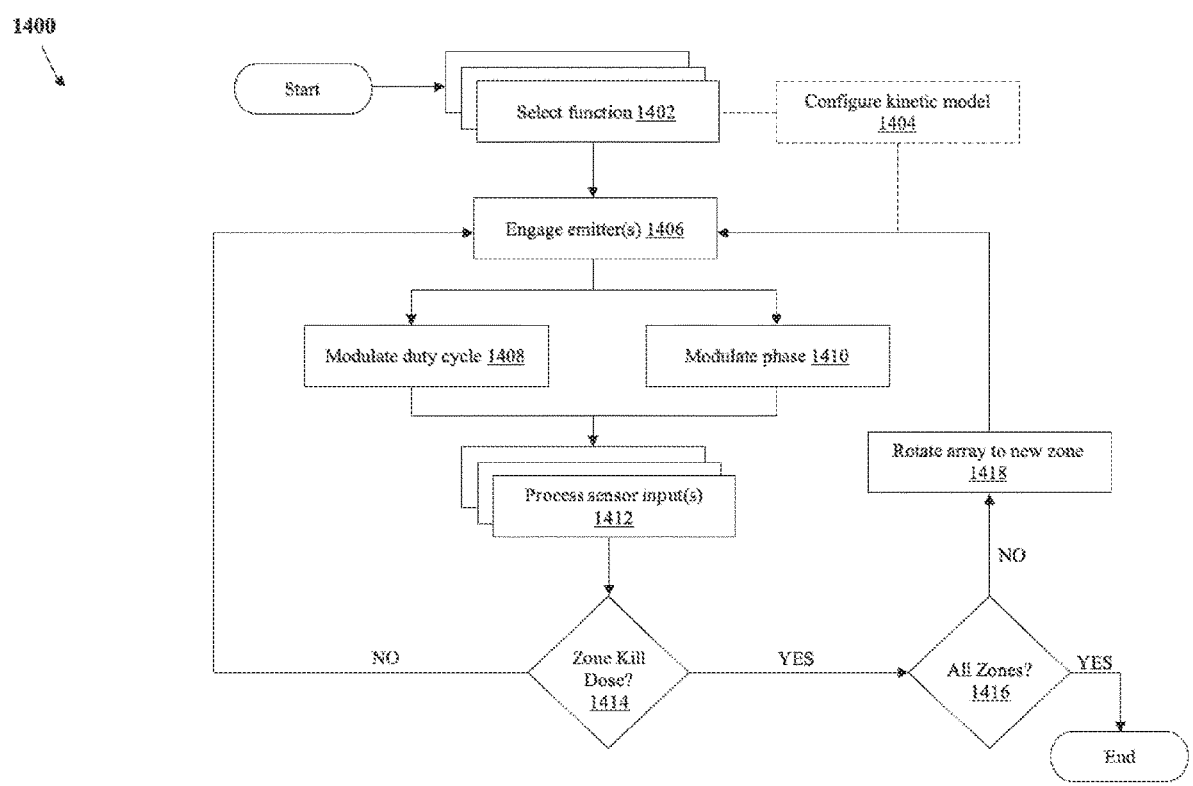
FIG. 14 is a functional block diagram of a routine for modulating a phase and duty cycle of at least one light emitting device, in accordance with an embodiment.

Referring now to FIG. 14 (with reference to FIG. 12), a functional block diagram of a routine 1400 for modulating a phase and duty cycle of at least one emitter within system 1200 is shown. In accordance with an embodiment, routine 1400 commences by selecting a function 1402 of system 1100; for example, selecting an operational mode or configuring a target dosing variable corresponding to a specific group or type of microorganism. Optionally, step 1402 may concurrently comprise configuring a kinetic model in response to, or in conjunction with, selecting the function of system 1200. In certain embodiments, step 1402 may comprise collecting data from one or more sensors to determine one or more situational or environmental conditions of an interior location for the purpose of configuring one or more control settings; for example, number of zones, emission settings, and the like. Routine 1400 may continue by engaging emitters in a one or more modes of operation 1406 to pulse an emission of radiation to a target surface within a target zone of emission. Routine 1400 may continue in step 1408 by modulating the duty cycle of UV emitters 1206 and/or near-UV emitters 1208; and may continue in step 1410 by modulating a phase of UV emitters 1206 and/or near-UV emitters 1208, such that UV emitters 1206 and near-UV emitters 1208 pulse emission in-phase according to a first modulation control and out of phase according to a second modulation control. Routine 1400 may continue by processing one or more sensor inputs 1412 (e.g., a closed-loop radiation sensor input and a ranging sensor input). Routine 1400 continues by executing decision steps 1414 and 1416. In decision step 1414, the controller processes the sensor input(s) to determine if a threshold dose of radiation (i.e. a kill dose) has been delivered to the target emission zone. If NO, routine 1400 continues by engaging emitters in accordance with step 1406. If YES, routine 1400 proceeds to decision step 1416. In decision step 1414, the controller processes the dosage data stored in memory to determine if a threshold dose of radiation (i.e. a kill dose) has been delivered to all target emission zones for the interior location. If YES, the controller stores the dosing data in memory (and optionally communicates the dosing data to one or more communicably engaged devices) and terminates emission 1418. If NO, routine 1400 continues to step 1418. Step 1408 is configured to engage the motor to rotate the array surface to the next or successive zonal orientation. Upon orienting the array surface to the relevant zonal orientation, routine 1400 continues by engaging emitters in accordance with step 1406 until all zones have received a threshold dose of radiation in accordance with the relevant kinetic model.

Other alternative embodiments of the present disclosure may provide for one or more fixed planar emitters and/or one or more rotational planar emitters. The configuration of fixed vs. planar emitters may depend on the desired disinfection application. For example, the hospital room application as discussed above employs a rotational planar emitter to reduce time disinfection time and overexposure of UV radiation; while an aircraft application employs multiple fixed planar emitters. A bathroom stall, by comparison, may employ a fixed and/or a rotational planar emitter.

Embodiments of the present disclosure provide for application-specific programming of disinfection zones; for example, "keep out" zones and target zones.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions (i.e., computer-executable instructions) may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s). Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrases are used herein, a processor may be "operable to" or "configured to" perform a certain function in a variety of ways, including, for example, by having one or more general-purpose circuits perform the function by executing particular computer-executable program code embodied in computer-readable medium, and/or by having one or more application-specific circuits perform the function.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." As used herein, the terms "right," "left," "top," "bottom," "upper," "lower," "inner" and "outer" designate directions in the drawings to which reference is made.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention.

What is claimed is:

1. A germicidal disinfection apparatus comprising:
   a housing assembly comprising a base housing and an array housing;
   a motor housed in the base housing and configured to rotate the array housing from at least one first orientation to at least one second orientation;
   a plurality of emitters comprising an array and housed in the array housing, the plurality of emitters comprising:
      at least one first emitter configured to emit ultraviolet light at a wavelength between 100 to 280 nanometers;
      at least one second emitter configured to emit visible light at a wavelength between 400 and 410 nanometers;
   a controller operably engaged with the plurality of emitters to modulate a duty cycle of the at least one first emitter and the at least one second emitter;
      wherein the controller comprises at least one processor and at least one non-transitory computer-readable medium having instructions stored thereon that, when executed, cause the processor to perform one or more operations, the one or more operations comprising:
      modulating a duty cycle of the at least one first emitter;
      modulating a duty cycle of the at least one second emitter; and
      modulating a pulse width of the at least one first emitter and the at least one second emitter such that the at least one first emitter and the at least one second emitter are configured to pulse emissions of ultraviolet light and visible light, respectively, in phase or out of phase; and
   at least one dual-band radiation sensor coupled to a surface of the housing assembly and communicably engaged with the controller.

2. The apparatus of claim 1 wherein the at least one first emitter and the at least one second emitter are configured to independently emit radiation in response to a control signal by the controller so as to produce a dual wavelength emission.

3. The apparatus of claim 1 wherein the one or more operations further comprise calculating a radiation dose delivered by the at least one first emitter and the at least one second emitter at one or more zonal orientation.

4. The apparatus of claim 1 further comprising at least one ranging sensor coupled to a surface of the housing assembly and communicably engaged with the controller.

5. The apparatus of claim 1 further comprising at least one orientation sensor communicably engaged with the controller.

6. The apparatus of claim 4 wherein the one or more operations further comprise modulating the duty cycle of the at least one first emitter and the at least one second emitter in response to an input from the at least one ranging sensor.

7. The apparatus of claim 1 wherein the one or more operations further comprise:
   calculating a radiation dose delivered by the at least one first emitter and the at least one second emitter in response to an input from the at least one dual-band radiation sensor; and
   engaging the motor to rotate the array housing from a first zonal orientation to a second zonal orientation.

8. The apparatus of claim 5 wherein the one or more operations further comprise determining one or more zonal orientation in response to an input from the at least one orientation sensor.

9. A method for controlling microorganisms in an interior environment comprising:
   positioning the germicidal disinfection apparatus of claim 1 in a first location of the interior environment;
   pulsing, in a first zonal orientation, an emission from the at least one first emitter and the at least one second emitter; and
   pulsing, in a second or subsequent zonal orientation, an emission from the at least one first emitter and the at least one second emitter.

10. The method of claim 9 further comprising modulating, with the controller, the pulse width of the at least one first emitter or the at least one second emitter according to a kinetic model associated with at least one bacteria, virus, or fungus, wherein the kinetic model comprises a dose-response curve for single band radiation and dual band radiation.

11. The method of claim 10 further comprising calculating, with the controller, the kinetic model according to one or more physical characteristics of the interior environment.

12. A germicidal disinfection apparatus comprising:
   a housing assembly comprising a base housing and an array housing;
   a motor housed in the base housing and configured to rotate the array housing 360 degrees around an axis;
   a plurality of emitters comprising an array of LEDs having a beam angle of less than or equal to 180 degrees, the plurality of emitters comprising:
      at least one first emitter configured to emit ultraviolet light at a wavelength between 100 to 280 nanometers;
      at least one second emitter configured to emit visible light at a wavelength between 400 and 410 nanometers;
   a controller operably engaged with the plurality of emitters to modulate a duty cycle of the at least one first emitter and the at least one second emitter;
      wherein the controller comprises at least one processor and at least one non-transitory computer-readable medium having instructions stored thereon that, when executed, cause the processor to perform one or more operations, the one or more operations comprising:
      modulating a duty cycle of the at least one first emitter;

modulating a duty cycle of the at least one second emitter;

modulating a pulse width of the at least one first emitter and the at least one second emitter such that the at least one first emitter and the at least one second emitter are configured to pulse emissions of ultraviolet light and visible light, respectively, in phase or out of phase; and engaging the motor to rotate the array housing between two or more zonal orientations;
wherein each zonal orientation in the two or more zonal orientations comprises an emission zone corresponding to the beam angle of the plurality of emitters; and at least one dual-band radiation sensor coupled to a surface of the housing assembly and communicably engaged with the controller.

13. The apparatus of claim 12 wherein the one or more operations further comprise calculating a radiation dose delivered by the at least one first emitter and the at least one second emitter in response to an input from the at least one dual-band radiation sensor.

14. The apparatus of claim 13 wherein the one or more operations further comprise engaging the motor to rotate the array housing between two or more zonal orientations in response to calculating the radiation dose.

15. A germicidal disinfection system comprising:
a germicidal disinfection apparatus comprising:
a housing assembly comprising a base housing and an array housing;
a motor being housed in the base housing and configured to rotate the array housing from a first zonal orientation to a second zonal orientation;
a plurality of emitters comprising an array and being housed in the array housing, the plurality of emitters comprising:
at least one first emitter configured to emit ultraviolet light at a wavelength between 100 to 280 nanometers;
at least one second emitter configured to emit visible light at a wavelength between 400 and 410 nanometers;
a controller being operably engaged with the plurality of emitters to modulate a duty cycle of the at least one first emitter and the at least one second emitter;
wherein the controller comprises at least one processor and at least one non-transitory computer-readable medium having instructions stored thereon that, when executed, cause the processor to perform one or more operations, the one or more operations comprising:
modulating a duty cycle of the at least one first emitter;
modulating a duty cycle of the at least one second emitter; and
modulating a pulse width of the at least one first emitter and the at least one second emitter such that the at least one first emitter and the at least one second emitter are configured to pulse emissions of ultraviolet light and visible light, respectively, in phase or out of phase;
at least one dual-band radiation sensor coupled to a surface of the housing assembly and communicably engaged with the controller; and
a mobile electronic device being communicably engaged with the controller to command one or more mode of operation of the germicidal disinfection apparatus.

16. The apparatus of claim 15 wherein the one or more mode of operation comprises modulating the duty cycle of the at least one first emitter and the at least one second emitter according to a kinetic model comprising an effective radiation kill dose for at least one bacteria, virus, or fungus, wherein the kinetic model comprises a dose-response curve for single band radiation and dual band radiation.

17. The apparatus of claim 15 wherein the one or more mode of operation comprises modulating a pulse width of the at least one first emitter and the at least one second emitter according to a kinetic model comprising an effective radiation kill dose for at least one bacteria, virus, or fungus, wherein the kinetic model comprises a dose-response curve for single band radiation and dual band radiation.

18. The apparatus of claim 15 wherein the one or more operations of the controller further comprise:
calculating a radiation dose delivered by the at least one first emitter and the at least one second emitter; and
engaging the motor to rotate the array housing from the first zonal orientation to the second zonal orientation.

* * * * *